United States Patent [19]

Uhlig et al.

[11] 4,408,631
[45] Oct. 11, 1983

[54] WEDGE-TYPE TAP FOR THE STERILE SAMPLING OF LIQUIDS

[76] Inventors: Klaus Uhlig, Apt. 2331 c/o Cerveceria Polar; Marian Szczurek, Calle Caurimare, Res. Los Tulipanes Apto. 52 Col.B.Monte; Carlos Vilacha, Av. Circunvalacion Del Sol, Res "46" Apto 42 Santa Paula, all of Caracas, Venezuela; Juergen Beckmann, 7410 Reutlingen, Fed. Rep. of Germany

[21] Appl. No.: 77,639

[22] Filed: Sep. 18, 1979

[30] Foreign Application Priority Data

Sep. 19, 1978 [DE] Fed. Rep. of Germany ..... 28407343

[51] Int. Cl.³ ............................................ F16K 27/08
[52] U.S. Cl. .................................. 137/380; 137/381; 251/144; 251/352
[58] Field of Search ............... 251/144, 310, 311, 349, 251/351, 352, 353, 114; 137/380, 381

[56] References Cited

U.S. PATENT DOCUMENTS

| 306,168 | 10/1884 | Moseley | 251/352 X |
| 680,447 | 8/1901 | Swedin | 251/352 |
| 1,663,952 | 3/1928 | Peaden | 251/353 X |
| 2,698,630 | 1/1955 | McShurley et al. | 251/352 X |
| 4,073,314 | 2/1978 | Speelman et al. | 251/368 X |

FOREIGN PATENT DOCUMENTS 647565 12/1950 United Kingdom ............... 251/144

Primary Examiner—A. Michael Chambers
Attorney, Agent, or Firm—Weingarten, Schurgin, Gagnebin & Hayes

[57] ABSTRACT

A faucet plug is disposed in a housing transversely to a tank wall so as to be rotatable about its longitudinal axis and is fixedly connected with its end portion outside of the tank to a bent discharge pipe, and a through-passage extends in the longitudinal axis of the faucet plug and terminates in a radial inlet portion which, when the discharge pipe is turned downwards, merges into the inlet opening of the housing. Preferably, at least one of the functional components is made of a self-sealing slidable plastics material and the other one is made of metal.

2 Claims, 3 Drawing Figures

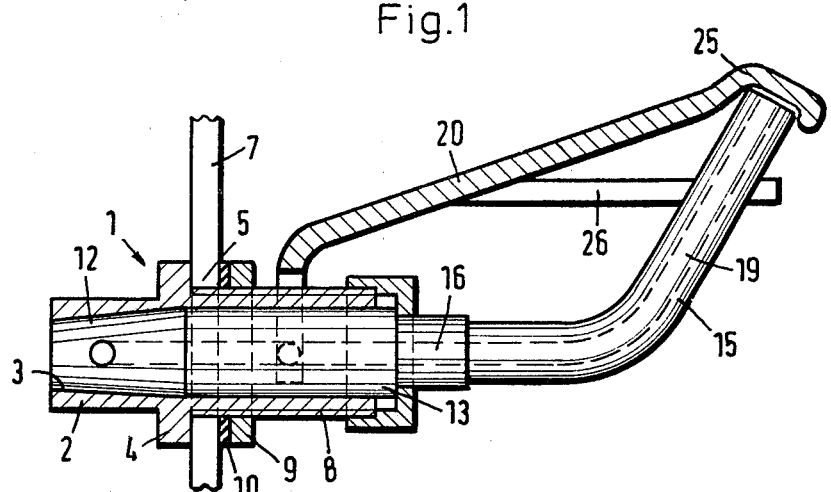
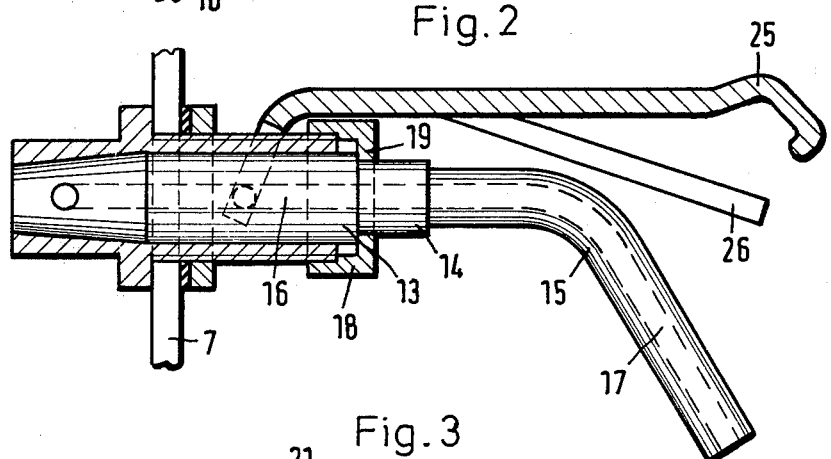
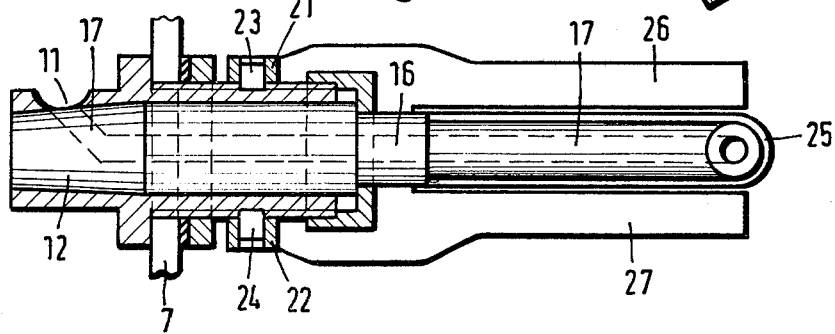

WEDGE-TYPE TAP FOR THE STERILE SAMPLING OF LIQUIDS

FIELD OF THE INVENTION

This invention concerns a wedge-type tap for the sterile sampling of liquids, especially of fermented beverages, including a tap housing sealingly mounted in a tank wall and having an inlet opening, a faucet plug disposed rotatably and in a liquid-tight manner in the housing and being retained therein by means of a screw cap and being provided with a through-passage, and further including a bent discharge pipe.

DISCUSSION OF THE PRIOR ART

The various fermentation processes in beverages like beers and wines, particularly the post-fermentation, take place in relatively large-sized pressure-tight, closed tanks or vats of steel (or lined steel), aluminum or reinforced concrete. Post-fermentation and the subsequent storage of the various types of beer takes between several weeks to some months, and during this period it is necessary to draw samples at predetermined time intervals for controlling the respective conditions. These controls relate to the intensity of the post-fermentation, the degree of fermentation, the concentration of carbon dioxide in beer, the fining, and the maturing with respect to palate, and above all to the biological condition of the beer. The post-fermentation and thus the release of carbon dioxide may be carried out by monitoring the bung device, whereas the internal processes in the storage tank can only be examined by drawing off samples through so-called wedge-type taps. In this connection the most important factor is the biological purity. Even slight bacterial infections, which on account of the low temperatures prevailing in the storage tanks do not affect the quality of the beer, may be a serious risk for the finished, bottled beer, because due to the higher storage temperatures in the public house or at the consumer's they may result in cloudiness and spoilage of the beer. For this reason the sampling must be conducted under sterile conditions so as to prevent contaminations or, for instance, oxygen contained in the air from getting into the storage tank by way of the wedge-type tap, particularly the various sealing surfaces of the same. On the other hand it has to be ensured that bacterial impurities which may possibly have formed in the tap itself or at the sealing surfaces thereof, do not get into the sample during sampling so as not to adulterate the results of the examination.

Commonly used wedge-type tapes for liquid sampling consist of a tap housing sealingly mounted in a vertical wall of the storage tank or vat and having a tapered transverse bore for receiving in a liquid-tight manner a vertically extending faucet plug. In the tapered portion of the faucet plug, which is fixedly connected to a handle, there are formed through-passages which in the open position of the faucet plug communicate with a usually bent discharge pipe. This discharge pipe is fixedly connected to the tap housing, which in most cases is a hollow body. What is detrimental in these known wedge-type taps is that the sealing surfaces of the tap between the tapered portion of the faucet plug and the taper opening in the tap housing are outside of the tank and at least at some points are in constant contact with the liquid in the tank. Thus, on turning the faucet plug for sampling purposes, a small amount of the liquid may enter between the sealing surfaces, and during the longer storage times between the individual samplings bacterial cultures may develop therefrom. During the next sampling and by means of the return motion of the faucet plug these bacterial cultures may either get into the sample and infect the same or they may get into the stored liquid. To sterilize the taps prior to each sampling by means of burning-out requires a comparatively high expenditure of time and labor and in any case cannot be employed in connection with those wedge-type taps in which individual components like sealing members are made of plastics material. Moreover, the manufacture of such wedge-type taps also requires great care, particularly as regards the machining of the tapered surfaces of the faucet plug and the receiving opening in the housing, which necessarily has a detrimental effect on the manufacturing costs of such taps.

SUMMARY OF THE INVENTION

It is the object of the invention to provide a wedge-type tap of the specified kind, which is of simple structure, is highly reliable in preventing contamination of the stored liquid as well as the drawn-off samples, and may readily be actuated.

The present invention accomplishes this object in that the faucet plug is disposed in the housing transversely to the tank wall so as to be rotatable about its longitudinal axis and is fixedly connected with its end portion outside of the tank to the bent discharge pipe, and that the through-passage extends in the longitudinal axis of the faucet plug and terminates in a radial inlet portion which, when the discharge pipe is turned downwards, merges into the inlet opening of the housing, and that at least one of the functional components is made of a self-sealing slidable plastics material and the other one is made of metal.

The structure of the wedge-type tap according to this invention, especially the combination of the faucet plug and the discharge pipe to form a unitary component part, offers the possibility that by turning of the bent discharge pipe into its downwardly pointing position the tap is opened for sampling purposes and that in the case of the discharge pipe being turned to face upwardly a sterile buffer liquid may be introduced into the tap, which liquid when it has a suitable viscosity will enter in very small amounts between the parting planes of the tapered faucet plug portion and will thus reliably prevent any growth of bacterial cultures or any other accumulation of even the smallest amounts of contaminants. This effect is enhanced by the fact that the tapered portion of the faucet plug is disposed within an inlet piece of the tap housing within the tank such that shutting-off already takes place in this region.

A further suitable development of this invention features a locking means, which prevents an inadvertent turning of the discharge pipe from its upwardly directed position and thus prevents escape of the buffer liquid and a possible opening of the wedge-type tap.

Advantageously, the locking means is designed as a strap pivotally mounted either on the housing or on the discharge pipe, one portion of the strap covering the mouth of the upwardly directed discharge pipe and including two fork-shaped tines extending on either side of the upwardly facing discharge pipe and preventing rotation thereof.

The strap may also be pivotally mounted direct on the discharge pipe and the inwardly directed fork-shaped end thereof may in the closed position surroundingly engage the tap housing on one side, wherein said tap housing in this portion has at least one flattened section as a safety means against turning.

BRIEF DESCRIPTION OF THE DRAWING

The objects, advantages and features of the invention will be more readily appreciated from the following detailed description when read in conjunction with the accompanying drawing in which:

FIG. 1 is a longitudinal sectional view of the wedge-type tap of the invention in closed position;

FIG. 2 shows the wedge-type tap of FIG. 1 during sampling; and

FIG. 3 is a horizontal axial section of the wedge-type tap in the position of FIG. 2.

DESCRIPTION OF THE PREFERRED EMBODIMENT

The wedge-type tap illustrated in the drawing comprises a substantially cylindrical housing 1 which on the side lying inside the tank includes an extension 2 having a conical inner surface 3 and an annular flange 4. The annular flange 4 engages the edge of the tank wall 7 in a liquid-tight manner. The portion of the housing protruding through the opening formed in the tank wall 7 carries external threads 8 onto which a lock nut 9 is threaded, the lock nut pressing a sealing disc 10 against the outer edge 5 of the tank wall 7. As is evident particularly from FIG. 3, a curved inlet opening 11 is formed in the extension 2 of the housing, which is provided inside the tank.

Within the tap housing 1, which is in part cylindrical and in part conical, a faucet plug is rotatably mounted and consists of a tapered portion 12 and a cylindrical portion 13. A bent discharge pipe 15 is either formed onto a cylindrical extension of the cylindrical portion 13 or connected to the faucet plug so as to be rotatable therewith. In the embodiment shown in the drawing, the faucet plug 12, 13 together with the extension 14 and the bent discharge pipe 15 is formed as an integral component of a self-sealing, slidable plastics material. The housing 2 is also unitary and is formed of metal. Basically, it is also possible to make the housing of a plastics material and the faucet plug of metal, or to make both functional members of the same material, i.e., either of metal or of plastics material, respectively.

In the longitudinal axis of the faucet plug 12, 13, which is disposed transversely to the tank wall 7, there is formed a through-passage 16 terminating into a radial, inclined inlet portion 7 in the frusto-conical portion of the faucet plug. The through-passage 16 extends continuously to the outlet passage 17' in the discharge pipe 15. The faucet plug and the discharge pipe are retained in the housing by means of a screw cap 18 threaded onto the end portion of the tap housing 2 provided outside of the tank, the screw cap by means of a radial flange 19 being pressed against the end portion of the cylindrical faucet plug portion 13 forming a shoulder.

As shown in FIG. 1, the discharge pipe 15 and the faucet plug 12, 13 integral therewith are filled, in the shutting-off position shown in the figure, with an inert buffer liquid 19, which in the condition shown in the drawing may enter in very small amounts between the sealing faces of the frusto-conical faucet plug portion 12 and the extension 2, thus preventing, if necessary by means of suitable chemical additives, the growth of bacteria.

In order to ensure the closed position of the wedge-type tap shown in FIG. 1 there is provided a locking means comprising a one-piece metal strap 20. At the downwardly bent end portion the strap 20 includes two legs 21, 22, which through locating pins 23, 24 engage in radial blind bores in the cylindrical portion of the tap housing 2 and thus serve as pivots for pivoting motions of the strap 20. The free end of the strap 20 defines a closing cap 25 covering the free opening of the discharge pipe in the closed position according to FIG. 1. For locking the discharge pipe and thus the wedge-type tap in the shutting-off position, two legs 26, 27 are formed on the strap 20 and engage around either side of the bent, obliquely upwardly extending portion of the discharge pipe 15, thus inhibiting any inadvertent rotary movements.

The invention is not limited to the embodiment shown and described above. In particular, the locking means may also be formed in such a manner that the strap is not pivoted to the tap housing but direct to the discharge pipe, while its bifurcated end disposed inside the tank surrounds and engages a flattened portion of the otherwise cylindrical tap housing 2. When the faucet plug 12, 13 together with the discharge pipe 15 is formed as a unitary structural member of plastics material, the sharp edge of the mouth of the inlet portion 17, which is formed by the inclined extension of this portion 17, may be arcuate as shown in FIG. 3 in order to avoid deformations resulting from the pressure exerted by the faucet plug and to ensure a highly uniform inflow of liqud. Furthermore, with a suitably designed housing the wedge-type tap may also be mounted in inclined or curved tank walls, so that in the rest position it will be in level engagement with the tank and will project far out from the tank for ease of sampling.

To ensure complete discharge of the disinfectant solution used as buffer liquid from the tap prior to sampling, it is furthermore contemplated to offset the radial inlet portion of the through-passage with respect to the bending direction of the discharge pipe by a few degrees such that in the horizontal position of the inlet portion the discharge pipe will be directed obliquely downwardly. Of course, in this position of the tap the communication with the tank interior will be shut off.

It would also be suitable not to offset the inlet portion with respect to the bent discharge pipe by an angle of about 90 degrees—as shown in the drawing—but instead to have it extend in approximately the same or the opposite direction. This would mean that yeast also cannot accumulate in the mouth of the inlet portion, because the latter would face downwardly.

It is likely that in view of the above description changes and improvements will occur to those skilled in the art which are within the scope of this invention. The invention is to by limited only be the appended claims.

What is claimed is:

1. A wedge-type tap for the sterile sampling of beer or wine contained in a tank, said tap comprising:
   a tap housing having a cylindrical longitudinal bore with a tapered end portion defining a frusto-conical surface, said housing being sealingly mounted transversely in a wall of the tank with the apex of the tapered end of the bore lying inside the tank, said housing having an inlet opening on one side of the tapered end inside the tank;
   a cylindrical faucet plug with a tapered end adapted to mate with the bore in the housing and formed with a through-passage extending in its longitudinal axis and terminating in a radial inlet portion within the tapered portion inside the tank, said faucet plug being arranged in said housing bore, being rotatable about its own longitudinal axis and having a further end portion extending from said housing;

a screw cap threaded to an outer cylindrical end portion of said faucet plug thereby securing said faucet plug to said housing in liquid-tight manner;

a bent discharge pipe fixedly connected to the outer end portion of said faucet plug, said radial inlet portion of the faucet plug being positioned longitudinally to connect with the inlet opening of said housing and providing a flow path from the tank through the discharge pipe when said discharge pipe is in its downward position, and said tapered end of the faucet plug sealing off the inlet opening of said housing when said discharge pipe is in its upward position;

said housing and said faucet plug consisting of a material selected from the group consisting of a metal and a self-sealing slidable plastics material; and a locking means designed as a strap pivotally mounted on said housing and having at its free end a cap for covering said discharge pipe, two legs being formed onto said strap which surroundingly engage the upwardly directed discharge pipe on either side whereby said locking means secures said discharge pipe in its upwardly directed position against inadvertent turning and covers the discharge opening of said discharge pipe.

2. The tap as recited in claim 1 wherein:

said through-passage in said faucet plug and said discharge pipe in its upwardly directed shutting-off position are adapted to be filled with an inert buffer liquid.

* * * * *